(12) United States Patent
Vite et al.

(10) Patent No.: US 7,211,593 B2
(45) Date of Patent: May 1, 2007

(54) C12-CYANO EPOTHILONE DERIVATIVES

(75) Inventors: Gregory D. Vite, Titusville, NJ (US); Alicia Regueiro-Ren, Middletown, CT (US)

(73) Assignee: Bristol-Myers Squibb Co., Princeton, NJ (US)

( * ) Notice: Subject to any disclaimer, the term of this patent is extended or adjusted under 35 U.S.C. 154(b) by 275 days.

(21) Appl. No.: 10/386,059

(22) Filed: Mar. 11, 2003

(65) Prior Publication Data

US 2003/0186965 A1 Oct. 2, 2003

Related U.S. Application Data

(60) Provisional application No. 60/363,703, filed on Mar. 12, 2002.

(51) Int. Cl.
*A61K 31/427* (2006.01)
*C07D 277/30* (2006.01)

(52) U.S. Cl. ............................... 514/365; 548/204

(58) Field of Classification Search .............. 548/204; 514/365
See application file for complete search history.

(56) References Cited

U.S. PATENT DOCUMENTS

| | | | |
|---|---|---|---|
| 6,194,181 B1 | 2/2001 | Hofmann et al. |
| 6,204,388 B1 | 3/2001 | Danishefsky et al. |
| 6,211,412 B1 | 4/2001 | Georg et al. |
| 6,242,469 B1 | 6/2001 | Danishefsky et al. |
| 6,262,094 B1 | 7/2001 | Hoefle et al. |
| 6,316,630 B1 | 11/2001 | Danishefsky et al. |
| 6,365,749 B1 | 4/2002 | Kim et al. |
| 6,369,234 B1 | 4/2002 | Danishefsky et al. |
| 6,380,227 B1 | 4/2002 | Mutz |
| 6,380,395 B1 | 4/2002 | Vite et al. |
| 6,399,638 B1 | 6/2002 | Vite et al. |
| 6,498,257 B1 | 12/2002 | Vite et al. |
| 6,576,651 B2 | 6/2003 | Bandyopadhyay et al. |
| 6,605,599 B1 | 8/2003 | Vite et al. |
| 6,670,384 B2 | 12/2003 | Bandyopadhyay et al. |

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| DE | 10020517 | * 10/2001 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |

(Continued)

OTHER PUBLICATIONS

U.S. Appl. No. 08/923,869, filed Sep. 4, 1997, Nicolaou et al.

(Continued)

*Primary Examiner*—Kamal A. Saeed
*Assistant Examiner*—Rebecca Anderson
(74) *Attorney, Agent, or Firm*—Anastasia P. Winslow

(57) ABSTRACT

The present invention relates to compounds useful in the treatment of cancer or other proliferative diseases represented by the formula

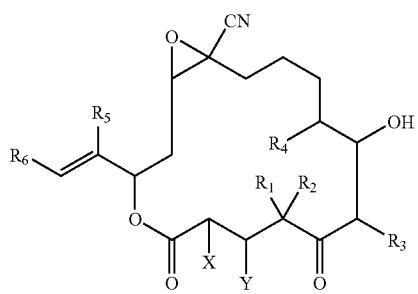

wherein:
$R_1$, $R_2$, $R_3$, $R_4$, $R_5$ are hydrogen or lower alkyl;
$R_6$ is selected from the group consisting of hydrogen, alkyl, substituted alkyl, aryl, substituted aryl, cycloalkyl, or heterocyclo;
X is hydrogen and Y is hydroxy, or X and Y taken together represent a carbon-carbon bond;
and pharmaceutically acceptable salts, solvates, or hydrates thereof.

Also included are therapeutic compositions containing the compounds represented by formula I as active ingredients, alone or in combination with other therapeutic agents useful in the treatment of cancer or other proliferative diseases.

19 Claims, No Drawings

FOREIGN PATENT DOCUMENTS

| WO | 99/42602 | 8/1999 |
|---|---|---|
| WO | 99/43320 | 9/1999 |
| WO | 99/43653 | 9/1999 |
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | 00/49021 | 8/2000 |
| WO | 0066589 | 11/2000 |
| WO | WO03/078411 | 9/2003 |

OTHER PUBLICATIONS

U.S. Appl. No. 60/032,864, filed Dec. 13, 1996, Nicolaou et al.
Balog, A., et al., "Total Synthesis of (-)-Epothilone A", *Angew. Chem. Int. Ed. Engl.*, vol. 35, No. 23/24, 2801-2803 (1996).
Bertini, F., et al., "Alkenes from Epoxides by Reductive Elimination with Magnesium Bromide-Magnesium Amalgam", *Chem. Commun.*, 144 (1970).
Bollag, D.M., et al., "Epothilones, A New Class of Microtubule-stabilizing Agents with a Taxol-like Mechanism of Action", *Cancer Res.* 55, No. 11, 2325-2333 (1995).
Fujisawa, T., et al., "Deoxygenation of Epoxides to Olefins with $FeCl_3$-n-BuLi System", *Chem. Lett.*, 883-886 (1974).
Fujiwara, Y., et al., "Reductive Coupling of Carbonyl Compounds to Olefins by Tungsten Hexachloride-Lithium Aluminum Hydride and Some Tungsten and Molybdenum Carbonyls", *J. Org. Chem.*, vol. 43, No. 12, 2477-2479 (1978).
Gladysz, J.A., et al., "Deoxygenation of Epoxides by Metal Atom Cocondensation", *J. Org. Chem.*, vol. 41, No. 22, 3647-3648 (1976).
Hofle, G., et al., "Epothilone A and B—Novel 16-Membered Macrolides with Cytotoxic Activity: Isolation, Crystal Structure, and Conformation in Solution", *Angew. Chem. Int. Ed. Engl.*, vol. 35, No. 13/14, 1567-1569 (1996).
Hofle, G., et al., "N-Oxidation of Epothilone A-C and O-Acyl Rearrangement to C-19 and C-21 -Substituted Epothilones", *Angew. Chem. Int. Ed.*, vol. 38, No. 13/14, 1971-1974 (1999).
Inokuchi, T., et al., "Opening of Epoxides to Olefins or Halohydrins with Vanadium(II)-Tetrahydrofuran or Vanadium(III)-Tetrahydrofuran Complexes", *Synlett*, No. 6, 510-512 (1992).
Kowalski, R. J., et al., "Activities of the Microtubule-stabilizing Agents Epothilones A and B with Purified Tubulin and in Cells Resistant to Paclitaxel (Taxol® )" *J. Biol. Chem.*, vol. 272, No. 4, 2534-2541 (1997).
Kupchan, S. M., et al., "Reductive Elimination of Epoxides to Olefins with Zinc-Copper Couple", *J. Org. Chem.*, vol. 36, No. 9, 1187-1190 (1971).
Martin, M. G., et al., "Epoxides as Alkene Protecting Groups. A Mild and Efficient Deoxygenation", *Tetrahedron Letters*, vol. 25, No. 3, 251-254 (1984).
McMurry, J. E., et al., "Reduction of Epoxides to Olefins with Low Valent Titanium", *J. Org. Chem.*, vol. 40, No. 17, 2555-2556 (1975).
McMurry, J. E., et al., "Some Deoxygenation Reactions with Low-Valent Titanium ($TiCl_3$/$LiAlH_4$)", *J. Org. Chem.*, vol. 43, No. 17, 3249-3254 (1978).
Meng, D., et al., "Remote Effects in Macrolide Formation Through Ring-Forming Olefin Metathesis: An Application to the Synthesis of Fully Active Epothilone Congeners", *J. Am. Chem. Soc.*, vol. 119, No. 11, 2733-2734 (1997).
Nicolaou, K. C., et al., "An Approach to Epothilones Based on Olefin Metathesis", *Angew. Chem. Int. Ed. Engl.*, vol. 35, No. 20, 2399-2401 (1996).
Nicolaou, K. C., et al., "Total Synthesis of Epothilone A: The Macrolactonization Approach", *Angew. Chem. Int. Ed. Engl.*, vol. 36, No. 5, 525-527 (1997).
Nicolaou, K. C., et al., "Designed Epothilones: Combinatorial Synthesis, Tubulin Assembly Properties, and Cytotoxic Action against Taxol-Resistant Tumor Cells", *Angew. Chem. Int. Ed. Engl.*, vol. 36, No. 19, 2097-2103 (1997).
Nicolaou, K. C., et al., "The Olefin Metathesis Approach to Epothilone A and Its Analogues", *J. Am. Chem. Soc.*, vol. 119, No. 34, 7960-7973 (1997).
Nicolaou, K. C., et al., "Total Syntheses of Epothilones A and B via a Macrolactonization-Based Strategy", *J. Am. Chem. Soc.*, vol. 119, No. 34, 7974-7991 (1997).
Nicolaou, K. C., et al., "Synthesis of Epothilones A and B in Solid and Solution Phase", *Nature*, vol. 387, 268-272 (1997).
Nicolaou, K. C., et al., "Synthesis of Epothilones A and B in Solid and Solution Phase" (Correction to *Nature* 387, 268-272)), *Nature*, 390, 100 (1997).
Raucher, S., et al., "Total Synthesis of (+)-Dihydrocostunolide via Tandem Cope-Claisen Rearrangement", *J. Org. Chem.*, vol. 51, No. 26, 5503-5505 (1986).
Sato, M, et al., "Reduction of Organic Compounds with Low-Valent Niobium ($NbCl_5$/$NaAlH_4$)", *Chem. Letters*, 157-160 (1982).
Schinzer, D., et al., "Total Synthesis of (-)-Epothilone A", *Agnew. Chem. Int. Ed. Engl.*, vol. 36, No. 5, 523-524 (1997).
Schobert, R., et al., "Reduction and Isomerization of Oxiranes and α-Diazoketones by Various Early Transition Metallocenes", *Synlett*, vol. 8, 465-466 (1990).
Sharpless, K. B., et al., "Lower Valent Tungsten Halides. A New Class of Reagents for Deoxygenation of Organic Molecules", *J. Amer. Chem. Soc.*, vol. 94, No. 18, 6538-6540 (1972).
Su, D.-S., et al., "Total Synthesis of (-)-Epothilone B: An Extension of the Suzuki Coupling Method and Insights into Structure-Activity Relationships of the Epothilones", *Angew. Chem. Int. Ed. Engl.*, vol. 36, No. 7, 757-759 (1997).
Su, D.-S., et al., "Structure-Activity Relationships of the Epothilones and the First In Vivo Comparison with Paclitaxel", *Angew. Chem. Int. Ed. Engl.*, vol. 36, No. 19, 2093-2096 (1997).
Victory, S. F., et al., "Relative Stereochemistry and Solution Conformation of the Novel Paclitaxel-Like Antimitotic Agent Epothilone A", *Bioorg. Med. Chem. Letts.*, vol. 6, No. 7, 893-898 (1996).
Winkler, J.D., et al., "A Model For The Taxol (Paclitaxel)/Epothilone Pharmacophore", *Bioorg. Med. Chem. Letts.*, vol. 6, No. 24, 2963-2966 (1996).
Yang, Z., et al., "Total Synthesis of Epothilone A: The Olefin Metathesis Approach", *Angew. Chem. Int. Ed. Engl.*, vol. 36, No. 1 / 2, 166-168 (1997).
Bollag, D., et al., "Epothilone, A New Structural Class of Microtubule Stabilizer", Abstract, *Proc. Am. Assoc. Cancer Res.*, vol. 36, 86 Meet. 454 (1995).
Bollag. D., "Epothilones: Novel Microtubule-Stabilising Agents", *Expert Opin. Invest. Drugs*, vol. 6, No. 7, 867-873 (1997).
Bertinato, P., et al., "Studies Toward a Synthesis of Epothilone A: Stereocontrolled Assembly of the Acyl Region and Models for Macrocyclization", J. Org. Chem., vol. 61, No. 23, 8000-8001 (1996).
*Chemical & Engineering News* "Epothilone Epiphany: Total Syntheses", vol. 74, No. 52, 24-26 (1996).
*Chemical & Engineering News*, "First Total Synthesis of Epothilone B", vol. 75, No. 13, 23 (1997).
*Chemical & Engineering News*, "Solid-Phase Epothilone Synthesis Used to Create Analog Library", vol. 75, No. 20, 33 (1997).
De Brabander, J., et al., "Towards a Synthesis of Epothilone A: Rapid Assembly of the C1-C6 and C7-C12 Fragments", *Synlett*, vol. 7, 824-826 (1997).
Gabriel, T. and Wessjohann, L., "The Chromium-Reformatsky Reaction: Asymmetric Synthesis of the Aldol Fragment of the Cytotoxic Epothilons from 3-(2-Bromoacyl)-2-Oxazolidinones", *Tetrahedron Lett.*, vol. 38, No. 8, 1363-1366 (1997).
Gerth, K., et al., "Epothilons A and B: Antifungal and Cytotoxic Compounds from *Sorangiusm cellulosum* (Myxobacteria) Production, Physico-chemical and Biological properties", *J. Antibiotics*, vol. 49, No. 6, 560-563 (1996).
Marshall, A., "Total Synthesis of Epothilone", *Nature Biotechnology*, vol. 15, No. 3, 205 (1997).
Meng, D., et al., "Studies Toward a Synthesis of Epothilone A: Use of Hydropyran Templates for the Management of Acyclic Stereochemical Relationships", *J. Org. Chem.*, vol. 61, No. 23, 7998-7999 (1996).

Meng, D., et al., "Total Syntheses of Epothilones A and B", *J. Am. Chem. Soc.*, vol. 119, No. 42, 10073-10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96-97 (1997).

Mulzer, J. and Mantoulidis, A., "Synthesis of the C(1)-C(9) Segment of the Cytotoxic Macrolides Epothilon A and B", *Tetrahedron Lett.*, vol. 37, No. 51, 9179-9182 (1996).

Nicolaou, K., et al., "Chemistry, Biology and Medicine of Selected Tubulin Polymerizing Agents", *Pure Appl. Chem.*, vol. 71, No. 6, 989-997 (1999).

Nicolaou, K., et al., "Total Synthesis of Epothilone E and Related Side-chain Modified Analogues Via a Stille Coupling Based Strategy", *Bioorg. Med. Chem.*, vol. 7, No. 5, 665-697 (1999).

Schinzer, D., et al., "Studies Towards the Total Synthesis of Epothilones: Asymmetric Synthesis of the Key Fragments", *Chem. Eur. J.*, vol. 2, No. 22, 1477-1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061-2064 (1997).

Schinzer, D., et al., "Syntheses of (-)-Epothilone A", *Chem. Eur. J.*, vol. 5, No. 9, 2483-2491 (1999).

Schinzer, D., et al., "Syntheses of (-)-Epothilone B", *Chem. Eur. J.*, vol. 5, No. 9, 2492-2500 (1999).

Nicolaou, K. C., et al., "Synthesis and Biological Properties of C12, 13-Cyclopropylepothilone A and Related Epothilones", *Chemistry & Biology*, vol. 5, No. 7, 365-372 (1998).

Altmann, K.H., et al., "Epothilones and Realted Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84-87 (1998).

Nicolaou et al., "Total Synthesis of Oxazole- and Cyclopropane-Containing Epothilone B Analogues by the Macrolactonization Approach", Chemistry, European Journal, vol. 3, No. 12, 1971-1986 (1997).

Nicolaou et al., "Chemical Biology of Epothilone", Angew. Chem. Int. Ed., 37, 2014-2045 (1988).

\* cited by examiner

C12-CYANO EPOTHILONE DERIVATIVES

CROSS-REFERENCE TO RELATED APPLICATION

This application claims priority from provisional application serial No. 60/363,703, filed Mar. 12, 2002, which is incorporated herein by reference in its entirety.

FIELD OF THE INVENTION

The present invention relates to 12-cyano substituted macrolide compounds possessing anti-tumor activity, methods for the preparation of these compounds, pharmaceutical compositions containing these compounds and methods of using the compounds.

BACKGROUND OF THE INVENTION

Epothilones are macrolide compounds which find utility in the pharmaceutical field. For example, Epothilones A and B having the structures:

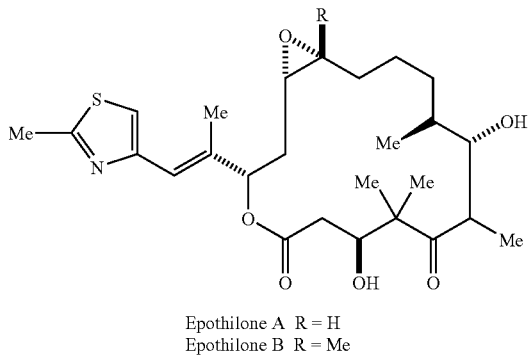

Epothilone A R = H
Epothilone B R = Me may be found to exert microtubule-stabilizing effects similar to paclitaxel (TAXOL®) and hence cytotoxic activity against rapidly proliferating cells, such as, tumor cells or other hyperproliferative cellular disease, see Hofle, G., et al., *Angew. Chem. Int. Ed. Engl.*, Vol. 35, No.13/14, 1567–1569 (1996); WO93/10121 published May 27, 1993; and WO97/19086 published May 29, 1997.

The widespread interest in epothilones that originated with the discovery of their mircotubulin-stabilization activity was furthered by the finding that epothilones were active in vitro against a number of paclitaxel-resistant human cancer cell lines (Bollag, D. M., et al., *Cancer Res.*, Vol. 55, 2325–2333 (1995); Kowalski, R. J., et al., *J. Biol. Chem.*, Vol. 272, 2534–2541 (1997)). Additionally, the relatively efficient total synthesis of epothilones, compared to that of paclitaxel, has lead to extensive efforts in the synthesis of epothilone analogs, as well as the characterization of their biological activity and structure/activity relationship (SAR) features. (Altmann, K.-H., et al., *Curr. Opin. Chem. Biol.*, Vol. 5, 424–431 (2001)).

Several groups have been active in this area including Danishefsky at the Memorial Sloan-Kettering Cancer Research Center, Nicolaou at the Scripps Research Institute, Altmann at Novartis Pharma AG and Klar at Shering AG. For example, the Danishefsky group has prepared and characterized the biological activity of 12,13-desoxyepothilone derivatives (Chou T.-C. et al., *Proc. Natl. Acad. Sci.*, Vol. 95, 9642 (1998)). The Nicolaou group at the Scripps Research Institute has synthesized 12,13-cyclopropyl, 12,13-cyclobutyl and related pyridine side-chain epothilone analogs. (Nicolaou, K. C., *J. Amer. Chem. Soc.*, Vol. 123, 9313–9323 (2001)). Epothilone derivatives containing 16-halo substitutions have been prepared by the group at Schering AG (WO 00/49021). Additionally, Altmann at Novartis Pharma AG has synthesized an epothilone analog in which the thiazole moitey is conformationally locked by a benzenoid functionality (Altmann, K. H. et al., *Chimica*, Vol. 54, No. 11,612–621 (2000)).

Derivatives and analogs of Epothilones A and B have been synthesized and may be used to treat a variety of cancers and other abnormal proliferative diseases. Such analogs are disclosed in Hofle et al., *Angew. Chem. Int. Ed. Engl.*, Vol. 35, No.13/14, 1567–1569 (1996); Nicolaou, K. C., et al., *Angew. Chem. Int. Ed. Engl.*, Vol. 36, No. 19, 2097–2103 (1997); Su, D. S., et al., *Angew. Chem. Int. Ed. Engl.*, Vol. 36, No. 19, 2093–2097 (1997); Su, D. S., et al., *Angew. Chem. Int. Ed. Engl.*, Vol. 36, 757–759 (1997); Meng, D., et al., *J. Amer. Chem. Soc.*, Vol. 119, 10073–10092 (1997); Yang, Z., et al., *Angew. Chem. Int. Ed. Engl.*, Vol. 36, 166–168 (1997); Nicolaou, K. C., et al., *Angew. Chem. Int. Ed. Engl.*, Vol. 36, 525–527 (1997); Nicolaou, K. C., et al., *Nature*, Vol. 387, 268–272 (1997); Schinzer, D., et al., *Angew. Chem. Int. Ed. Engl.*, Vol. 36, 523–524 (1997); and Nicolaou, K. C., et al., *Angew. Chem. Int. Ed. Engl.*, Vol. 37, 2014–2045 (1998).

Although natural product epothilones A and B have shown excellent in vitro cytotoxic activity against cancer cell lines, difficulties remain with respect to their in vivo use due to a lack of stability, including metabolic stability, and potential toxicity (Lee, F., et al., *Clin. Can. Res.*, Vol. 7, 1429–1437 (2001)). Thus, there remains a need in the art for biologically active epothilone compounds with improved in vivo stability and improved safety profiles.

SUMMARY OF THE INVENTION

The present invention is directed to epothilone compounds possessing anti-proliferative and anti-neoplastic activity, including chemically and thermally stable compounds. The invention further encompasses pharmaceutical compositions and methods for the treatment and prevention of primary or metastatic cancer utilizing the compounds of the invention. The compounds of the present invention are particularly useful for treating or preventing proliferative diseases, particularly cancers responsive to microtubule-stabilization agents. Thus, the invention further comprises treating or preventing diseases or disorders through microtubule-stabilization by contacting cells in need thereof with compounds of the present invention.

In one embodiment, the invention relates to compounds which are referred to herein as "12-cyano epothilone derivatives" having the following formula:

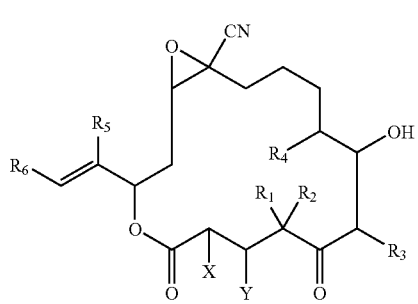

I wherein:

$R_1$, $R_2$, $R_3$, $R_4$, $R_5$ are hydrogen or lower alkyl;

$R_6$ is selected from the group consisting of hydrogen, alkyl, substituted alkyl, aryl, substituted aryl, cycloalkyl, or heterocyclo;

X is hydrogen and Y is hydroxy, or X and Y taken together represent a carbon-carbon bond;

and isomers, clathrates, prodrugs, pharmaceutically acceptable salts, solvates or hydrates thereof.

In another embodiment, the present invention relates to methods for treating a variety of conditions by administering a therapeutically or prophylactically effective amount of a compound of formula (I) to an animal, preferably a mammal, especially a human subject in need thereof (referred to herein as a "patient"). Prior to administration, one or more compounds of this invention are typically formulated as a pharmaceutical composition which contains an effective dosage amount of one or more of such compounds in combination with one (or more) pharmaceutically acceptable carrier(s) or vehicle(s).

In another embodiment, the present invention is directed to methods of inducing microtubule-stabilization in mammalian cells by contacting the cells with a compound of the present invention.

Conditions that may be treated or prevented by the compounds of this invention, or a pharmaceutical composition thereof, include but are not limited to primary cancers, metastatic cancers, solid tumors, and blood-borne tumors. In one embodiment, the present invention is directed to methods of treating and/or preventing cancers of the brain, breast, central nervous system, stomach, bladder, prostate, colon, rectum, liver, lung (both small cell and non-small cell), pancreas, esophagus, mouth, pharynx, kidney, bone, pituitary, ovary, uterine, skin, head and neck, cervix and larynx.

In another embodiment, the present invention further provides pharmaceutical compositions comprising a therapeutically effective or a prophylactically effective amount of one or more compounds of the invention and a pharmaceutically acceptable carrier or vehicle. A pharmaceutically acceptable carrier or vehicle can comprise an excipient, diluent, or a mixture thereof.

The compounds and pharmaceutical compositions described herein could also be useful in combination therapy with other anti-cancer/cytoxic agents, angiogenesis inhibitors, anti-cancer vaccines and antibody based treatments. Additionally, the compounds and pharmaceutical compositions described herein could be useful as an adjunct to existing and/or experimental therapies. The compounds of the present invention can also used in combination with chemotherapy or irradiation therapy.

Methods of administration include but are not limited to oral, parenteral, mucosal and topical; such modes of administration further include intramuscular, intraperitoneal, intravenous, subcutaneous, intracerebral, epidural, sublingual, buccal, rectal, vaginal, intranasal, intraocular, oral, and transdermal. Preferably, the pharmaceutical compositions are formulated for injection. Preferably, oral administration will be in combination with an antacid or other suitable buffer effective at neutralizing the acidity of the stomach.

These and other aspects of this invention will be evident upon reference to the following detailed description. To that end, certain patent and other documents are cited herein to more specifically set forth various aspects of this invention. Each of these documents are hereby incorporated by reference in their entirety.

DETAILED DESCRIPTION OF THE INVENTION

The Compounds

It has been found in accordance with the present invention that the stability of certain analogs of the naturally-occurring epothilones are enhanced by having a cyano group at position 12 in place of the hydrogen or methyl groups shown in the above structures for epothilone A and B, respectively. In certain embodiments, the present invention is directed to any epothilone analog or derivative which may be stabilized by a 12-cyano group. Examples of such epothilone analogs or derivatives may be found in the following U.S. Pat. Nos. 4,272,525; 4,820,695; 5,545,624; 5,610,178; 5,677,287; 5,716,939; 5,760,011; 6,034,070; 6,090,601; 6,121,029; 6,124,453; 6,204,388; 6,211,412; 6,262,094; and 6,291,684, each of which is incorporated in its entirety by reference herein. Additional examples may be found in International Publication Nos. WO 00/43320, WO 00/01701, WO 00/01702, WO 00/23452, WO 00/26349, WO 00/31247, WO 00/37473, WO 00/39276, WO 00/47584, WO 00/49019, WO 00/49020, WO 00/49021, WO 00/50423, WO 00/57874, WO 00/63224, WO 00/63225, WO 00/66589, WO 00/71521, WO 00/71556, WO 01/07439, WO 01/09113, WO 01/27308, WO 96/09312, WO 92/19247, WO 93/10121, WO 94/21657, WO 95/02594, WO 96/26182, WO 97/19086, WO 97/38009, WO 98/02460, WO 98/03662, WO 98/08505, WO 98/08849, WO 98/22461, WO 98/24427, WO 98/25929, WO 98/38192, WO 98/47891, WO 98/54966, WO 99/01124, WO 99/02514, WO 99/03848, WO 99/03849, WO 99/07692, WO 99/12906, WO 99/16416, WO 99/27890, WO 99/43653, WO 99/44619, WO 99/54318, WO 99/54319, WO 99/54330, WO 99/58534, WO 99/61599, WO 99/65884, WO 99/65913, WO 99/66028, WO 99/67252 and WO 99/67253, each of which is incorporated in its entirety by reference herein. Examples of 12-cyano epothilone compounds and their preparation are provided below.

In a preferred embodiment, the present invention provides 12-cyano compounds having the general formula:

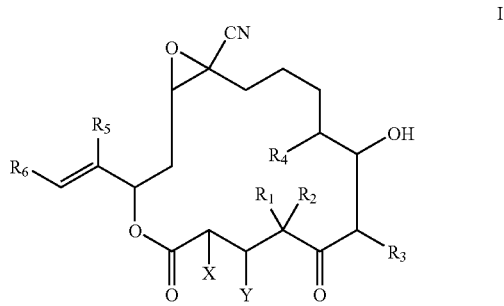

wherein:

$R_1$, $R_2$, $R_3$, $R_4$, $R_5$ are hydrogen or lower alkyl;

$R_6$ is selected from the group consisting of hydrogen, alkyl, substituted alkyl, aryl, substituted aryl, cycloalkyl, or heterocyclo;

X is hydrogen and Y is hydroxy, or X and Y taken together represent a carbon-carbon bond;

and isomers, clathrates, prodrugs, pharmaceutically acceptable salts, solvates or hydrates thereof.

In a further preferred embodiment, the present invention provides 12-cyano compounds having the general formula II:

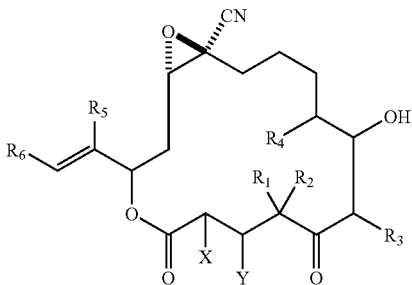

wherein:

$R_1$, $R_2$, $R_3$, $R_4$, $R_5$ are hydrogen or lower alkyl;

$R_6$ is selected from the group consisting of hydrogen, alkyl, substituted alkyl, aryl, substituted aryl, cycloalkyl, or heterocyclo;

X is hydrogen and Y is hydroxy, or X and Y taken together represent a carbon-carbon bond;

and isomers, clathrates, prodrugs, pharmaceutically acceptable salts, solvates or hydrates thereof.

The following are definitions of various terms used to describe this invention. These definitions apply to the terms as they are used throughout this specification, unless otherwise limited in specific instances, either individually or as part of a larger group.

The term "alkyl" refers to optionally substituted straight- or branched-chain saturated hydrocarbon groups having from 1 to 20 carbon atoms, preferably from 1 to 7 carbon atoms. The expression "lower alkyl" refers to optionally substituted alkyl groups having from 1 to 4 carbon atoms.

The term "substituted alkyl" refers to an alkyl group substituted by one or more substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "alkenyl" refers to optionally substituted unsaturated aliphatic hydrocarbon groups having from one to nine carbons and one or more double bonds. Substituents may include one or more substituent groups as described above for substituted alkyl.

The term "halogen" or "halo" refers to fluorine, chlorine, bromine and iodine.

The term "aryl" refers to monocyclic or bicyclic aromatic hydrocarbon groups having from 6 to 12 carbon atoms in the ring portion, for example, phenyl, naphthyl, biphenyl and diphenyl groups, each of which may be substituted.

The term "aralkyl" refers to an aryl group bonded to a larger entity through an alkyl group, such as benzyl.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "cycloalkyl" refers to optionally substituted saturated cyclic hydrocarbon ring systems, preferably containing 1 to 3 rings and 3 to 7 carbons per ring, which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached to a larger molecule at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "heterocycle," "heterocyclic," and "heterocyclo" include one or more substituent groups as described above for substituted alkyl or substituted aryl, and smaller heterocyclos, such as, epoxides, aziridines and the like.

The term "alkanoyl" refers to —C(O)-alkyl.

The term "substituted alkanoyl" refers to —C(O)-substituted alkyl.

The term "aroyl" refers to —C(O)-aryl.

The term "substituted aroyl" refers to —C(O)-substituted aryl.

The term "trialkylsilyl" refers to —Si(alkyl)$_3$.

The term "aryl dialkylsilyl" refers to —Si(alkyl)$_2$ (aryl).

The term "diaryl alkylsilyl" refers to —Si(aryl)$_2$ (alkyl).

The term "heteroatoms" shall include oxygen, sulfur and nitrogen.

The compounds of the invention, particularly of formula I, form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others (e.g., nitrates, phosphates, borates, tartrates, citrates, succinates, benzoates, ascorbates, salicylates and the like). Such salts are formed by reacting a compound represented by formula I in an equivalent amount of the acid in a medium in which the salt precipitates or in an aqueous medium followed by evaporation.

The compounds represented by formula I may also form salts with alkali metals such as sodium, potassium and lithium, with alkaline earth metals such as calcium and magnesium, with organic bases such as dicyclohexylamine and tributylamine, with pyridine and amino acids such as arginine, lysine and the like. Such salts can be obtained, for example, by exchanging carboxylic acid protons, if present in a compound represented by formula I, with the desired ion in a medium in which the salt precipitates or in an aqueous medium followed by evaporation. Other salts can be formed as known to those skilled in the art.

In addition, zwitterions ("inner salts") can be formed and are included within the term salts as used herein.

Prodrugs and solvates of the compounds represented by formula I are also contemplated herein. The term prodrug, as used herein, denotes a compound which, upon administration to a subject, undergoes chemical conversion by metabolic or chemical processes to yield a compound represented by formula I, or a salt and/or solvate thereof. For example, compounds represented by formula I may form a carboxylate ester moiety that may be hydrolyzed after ingestion. The carboxylate esters are conveniently formed by esterifying any of the carboxylic acid moieties present on the molecule. Solvates of the compounds of formula I are preferably hydrates.

Various forms of prodrugs are well known in the art and have been extensively reviewed in the literature. Such prodrug delivery derivatives are discussed, for example, in the following:

a) *Design of Prodrugs*, H. Bundgaard (editor), Elsevier (1985);

b) *Methods in Enzymology*, K. Widder et al. (editors), Academic Press, Vol. 42, 309–396 (1985);

c) *A Textbook of Drug Design and Development*, Krosgaard-Larsen and H. Bundgaard (editors), Chapter 5, "Design and Application of Prodrugs," 113–191 (1991);

d) H. Bundgaard, *Advanced Drug Delivery Reviews*, 8, 1–38 (1992);

e) H. Bundgaard, *J. of Pharm. Sciences*, 77, 285 (1988); and f) N. Kakeya et al., *Chem. Pharm. Bull.*, 32 692 (1984).

The compounds of the invention may exist as multiple optical, geometric, and stereoisomers. While the compounds shown herein are depicted for one optical orientation, included within the present invention are all isomers and mixtures thereof.

Preferred compounds represented by formula I:

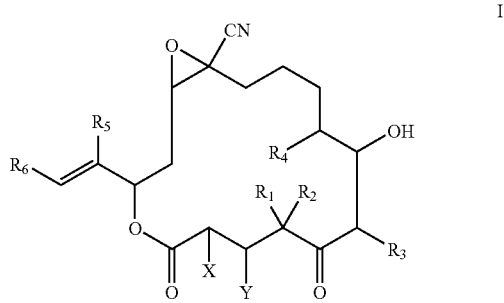

are those wherein:

$R_1$, $R_2$, $R_3$, $R_4$, $R_5$ are methyl;

$R_6$ is a heterocyclic group as defined herein including but not limited to:

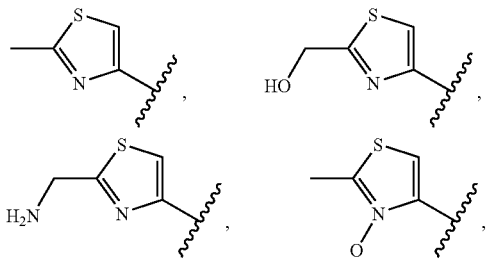

pyrrolidinyl, pyrrolyl, indolyl, pyrazolyl, imidazolyl, oxazolyl, oxazolidinyl, thiazolyl, furyl, thienyl, piperidinyl, piperazinyl, azepinyl, pyridyl, pyrazinyl, pyrimidinyl, morpholinyl, thietanyl, thiiranyl, triazinyl, and triazolyl;

X is hydrogen and Y is hydroxy;

and isomers, clathrates, prodrugs, pharmaceutically acceptable salts, solvates or hydrates thereof.

Pharmaceutical Compositions and Formulations

The present invention also provides pharmaceutical compositions comprising at least one of the compounds of the invention such as a compound represented by formula I capable of treating cancer or other proliferative diseases in an amount effective therefor, and a pharmaceutically acceptable carrier or vehicle. The compositions of the present invention may contain other therapeutic agents as described below, and may be formulated, for example, by employing conventional solid or liquid carriers or vehicles, as well as pharmaceutical additives of a type appropriate to the mode of desired administration, such as excipients, binders, preservatives, stabilizers, flavors, and the like according to techniques well known in the art of pharmaceutical formulation or called for by accepted pharmaceutical practice. The compounds represented by formula I can also be formulated in compositions such as sterile solutions or suspensions for parenteral administration. About 0.1 to 500 mg of a compound represented by formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The phrase "pharmaceutically acceptable salt(s)," as used herein includes but are not limited to salts of acidic or basic groups that may be present in compounds used in the present methods and compositions.

Exemplary compositions for oral administration include suspensions which may contain, for example, microcrystalline cellulose for imparting bulk; alginic acid or sodium alginate as a suspending agent; methylcellulose as a viscosity enhancer; sweeteners, such as fructose, aspartame or saccharin; flavoring agents, such as peppermint, oil of wintergreen; coloring agents; and preserving agents, to provide a pharmaceutically palatable preparation. Immediate release tablets which may contain, for example, one or more of microcrystalline cellulose, dicalcium phosphate, starch, magnesium stearate, lactose and other art-recognized excipients, binders, extenders, disintegrants, diluents and lubricants. Molded tablets, compressed tablets or freeze-dried tablets are exemplary forms that may be used. Exemplary compositions include those formulating the present compound(s) with fast-dissolving diluents such as mannitol, lactose, sucrose and cyclodextrins. Also included in such formulations may be high molecular weight excipients such as microcrystalline celluloses, polyethylene glycols (PEG) and the like. Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez®, available from Aldrich®), and agents to control release such as polyacrylic copolymer, carbopol and the like. Art-recognized lubricants, glidants, flavors, coloring agents and stabilizers may also be added for ease of fabrication and use. Additionally, where in tablet or pill form, the compositions may be coated to delay disintegration and absorption in the gastrointestinal tract thereby providing a sustained action over an extended period of time. Preferably, oral compositions are co-administered with an antacid to aid in neutralizing gastrointestinal fluids to prevent decomposition of the active compound(s). Selectively permeable membranes surrounding an osmotically active driving compound are also suitable for orally administered compounds or pharmaceutical compositions. In these later platforms, fluid from the environment surrounding the capsule is imbibed by the driving compound, which swells to displace the agent or agent composition through an aperture. These delivery platforms can provide an essentially zero-order delivery profile as opposed to the spiked profiles of immediate release formulations. A time delay material such as glycerol monostearate or glycerol stearate may also be used.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, including surfactants such as polyoxyethylated caster oil, Cremphor EL®, polysorbate 80, mannitol, 1,3-butanediol, polyethylene glycol, ethanol, water, Ringer's solution, Lactated Ringer's Solution, dextrose solutions, saline solutions such as isotonic sodium chloride solution, or other suitable dispersing or wetting and suspending agents, including synthetic mono- or diglycerides, and fatty acids, including oleic acid and the like. In one embodiment, immediately before use a compound of the present invention is reconstituted in either Sterile Water for Injection, USP, 5% Dextrose in Water ($D_5W$) or 0.9% Sodium Chloride for Injection, USP.

Exemplary compositions for rectal administration include suppositories which may contain, for example, a suitable non-irritating excipient, such as cocoa butter, synthetic glyceride esters or polyethylene glycols, which are solid at ordinary temperature, but liquify and/or dissolve in the rectal cavity to release the drug.

Exemplary compositions for topical administration include a topical carrier such as Plastibase® (mineral oil gelled with polyethylene available from Bristol-Myers Squibb Company). For example, the compounds of the invention may be administered topically to treat plaques associated with psoriasis and as such may be formulated as a cream or ointment.

When administered to a patient, the compounds are preferably in isolated form. By "isolated" it is meant that prior to administration, the compound is separated from other components of a synthetic organic chemical reaction mixture or natural product source. Preferably, the compounds are isolated via conventional techniques, e.g., extraction followed by chromatography, recrystalization, or another conventional technique.

Uses and Utility of the Compounds

The invention provides methods of treatment and/or prevention of cancers by administration to a patient a therapeutically or prophylactically effective amount of the compounds of the present invention or a pharmaceutically acceptable salt thereof.

The term "therapeutically effective amount" means the amount of a compound of the invention that will elicit the biological or medical response desired by the veterinarian or clinician that is treating diseases in the patient.

The term "prophylactically effective amount" means the amount of a compound of the present invention that will prevent or inhibit affliction or mitigate affliction of a patient with a medical condition that a veterinarian or clinician is trying to prevent, inhibit, or mitigate. Without being limited by any particular theory, the compounds of the invention, and in particular those of formula I, are believed to be primarily microtubule-stablizing agents. The compounds of the invention are useful for the treatment of a variety of cancers and other proliferative diseases including, but not limited to, the following:

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, xenoderma pigmentosum, tetratocarcinoma, keratoactanthoma, neuroblastoma, thyroid follicular cancer and glioma;

tumors of the central and peripheral nervous system, including astrocytoma, neuroblastoma, glioma, and schwannomas.

Compounds of the present invention are also useful in treating or preventing cancers of the brain, breast, central nervous system, stomach, bladder, prostate, colon, rectum, liver, lung (both small cell and non-small cell), pancreas, esophagus, mouth, pharynx, kidney, bone, pituitary, ovary, uterine, skin, head and neck, cervix and larynx.

Compounds represented by formula I will also inhibit angiogenesis, thereby affecting the growth of tumors and providing treatment of tumors and tumor-related disorders. Such anti-angiogenesis properties of the compounds represented by formula I will also be useful in the treatment of other conditions responsive to anti-angiogenesis agents including, but not limited to, certain forms of blindness related to retinal vascularization, arthritis, especially inflammatory arthritis, multiple sclerosis, restinosis and psoriasis.

Compounds of the invention as represented by formula I will induce or inhibit apoptosis, a physiological cell death process critical for normal development and homeostasis. Alterations of apoptotic pathways contribute to the pathogenesis of a variety of human diseases. Compounds represented by formula I, as modulators of apoptosis, will be useful in the treatment of a variety of human diseases with aberrations in apoptosis including, but not limited to, cancer and precancerous lesions, immune response related diseases, viral infections, degenerative diseases of the musculoskeletal system and kidney disease.

Without wishing to be bound to any mechanism or morphology, compounds of the invention may also be used to treat conditions other than cancer or other proliferative diseases. Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and cancer pain.

The present invention thus provides a method of treating an animal, preferably mammals and especially humans, in need of treatment for any of the aforementioned conditions, especially cancer or other proliferative diseases, comprising the step of administering to a subject in need thereof an effective amount of at least one compound represented by formula I. Other therapeutic agents such as those described below may be employed with the inventive compounds in the present method. In the method of the present invention, such other therapeutic agent(s) may be administered prior to, simultaneously with or following the administration of the compound(s) of the present invention.

Compounds of the present invention may be administered to patients who are either currently undergoing chemotherapy as well as those not undergoing chemotherapy. Compounds of the present invention may also be administered to patients who have previously undergone chemotherapy as well as those who have never undergone chemotherapy. Compounds of the present invention may be administered to patients who are either currently undergoing irradiation therapy as well as those not undergoing irradiation therapy. Compounds of the present invention may also be administered to patients who have previously undergone irradiation therapy as well as those who have never undergone irradiation therapy.

The effective amount of a compound of the present invention may be determined by methodologies well known to those skilled in the art and includes exemplary dosage amounts for a human of from about 0.05 to 200 mg/kg/day, which may be administered in a single dose or in the form of individual divided doses given, for example, up to four times per day. Preferably, the compounds are administered in a dosage of less than 100 mg/kg/day, in a single dose or in 2 to 4 divided doses. It will be understood that the specific dose level and frequency of dosage for any particular subject may be varied and will depend upon a variety of factors recognized by those skilled in the art including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammals, and especially humans.

Typically, the compounds of the present invention are administered until the patient shows a response, for example, a reduction in tumor size, or until dose-limiting toxicity is observed. One of ordinary skill in the art will readily know when a patient shows a response or when dose-limiting toxicity is reached. The common dose limiting toxicities associated with compounds of formulae I and II include, but are not limited to, fatigue, arthralgia/myalgia, anorexia, hypersensitivity, neutropenia, thrombocytopenia, and neurotoxicity.

In one embodiment, the compounds of the present invention are administered by IV infusion over a period of from about 10 minutes to about 3 hours, preferably about 30 minutes to about 2 hours, more preferably about 45 minutes to 90 minutes, and most preferably about 1 hour. In particular, the methods of the invention encompass dosing protocols such as once a day for 2 to 10 days, preferably every 3 to 9 days, more preferably every 4 to 8 days and most preferably every 5 days. In one embodiment there is a period of 3 days to 5 weeks, preferably 4 days to 4 weeks, more preferably 5 days to 3 weeks, and most preferably 1 week to 2 weeks, in between cycles where there is no treatment. In another embodiment compounds of the present invention can be administered orally, intravenously, or both, once a day for 3 days, with a period of preferably 1 week to 3 weeks in between cycles where there is no treatment. In yet another embodiment compounds of the present invention can be administered orally, intravenously, or both, once a day for 5 days, with a period of preferably 1 week to 3 weeks in between cycles where there is no treatment.

In one preferred embodiment the treatment cycle for administration of compounds of the present invention is once daily for 5 consecutive days and the period between treatment cycles is from 2 to 10 days, preferably one week.

Compounds of the present invention can also be administered orally, intravenously, or both once every 1 to 10 weeks, preferably every 2 to 8 weeks, more preferably every 3 to 6 weeks, and even more preferably every 3 weeks. In one embodiment, compounds of the present invention are administered once every week. In another embodiment, compounds of the present invention are administered once every 3 weeks.

The compounds of the invention may be administered either alone or in combination with other anti-cancer and cytotoxic agents and treatments useful in the treatment of cancer or other proliferative diseases. Such agents may be administered simultaneously or sequentially with the compounds represented by formula I. Especially useful are anti-cancer and cytotoxic drug combinations wherein the second drug chosen acts in a different manner or different phase of the cell cycle, e.g., S phase, than the present compounds of formula I which exert their effects at the $G_2$-M phase. Example classes of anti-cancer and cytotoxic agents include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, bleomycin A2, bleomycin B2, peplomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A-F or their analogs or derivatives; plant-derived products, such as vinca alkaloids, epipodophyllotoxins, taxanes; and topoisomerase inhibitors (e.g., irinotecan); prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with chemotherapy or irradiation therapy.

Representative examples of these classes of anti-cancer/cytotoxic agents include, but are not limited to, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, Chloroambucil, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, thiotepa, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenolic acid, daunorubicin, deferoxamine, floxuridine, doxifluridine, ratitrexed, idarubicin, epirubican, pirarubican, zorubicin, mitoxantrone, bleomycin sulfate, mitomycin C, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, verapamil, VP-16, altretamine, thapsigargin, topotecan and any analogs or derivatives thereof.

Further representative examples of these anti-cancer/cytotoxic agents include, but are not limited to, docetaxel (Taxotere®), trastuzumab (Herceptin®), cetuximab (Erbitux®) and gefitinib (Iressa®). These agents also can be used in the methods and pharmaceutical compositions of the present invention.

Preferred members of the classes of anti-cancer/cytotoxic agents discussed above include, without intended limitation, paclitaxel, cisplatin, carboplatin, doxorubicin, doxorubicin hydrochloride, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Further examples of anti-cancer and other cytotoxic agents include the following: epothilone derivatives as found in German Patent No. 4138042.8 and PCT International Publication Nos. WO 97/19086, WO 98/22461, WO 98/25929, WO 98/38192, WO 99/02224, WO 99/02514, WO 99/03848, WO 99/07692, WO99/27890, WO 00/43320, WO 00/01701, WO 00/01702, WO 00/23452, WO 00/26349, WO 00/31247, WO 00/37473, WO 00/39276, WO 00/47584, WO 00/49019, WO 00/49020, WO 00/49021, WO 00/50423, WO 00/57874, WO 00/63224, WO 00/63225, WO 00/66589, WO 00/71521, WO 00/71556, WO 01/07439, WO 01/09113, WO 01/27308, WO 96/09312, WO 92/19247, WO 93/10121, WO 94/21657, WO 95/02594, WO 96/26182, WO 97/38009, WO 98/02460, WO 98/03662, WO 98/08505, WO 98/08849, WO 98/24427, WO 98/47891, WO 98/54966, WO 99/01124, WO 99/03849, WO 99/07692, WO 99/12906, WO 99/16416, WO 99/43653, WO 99/44619, WO 99/54318, WO 99/54319, WO 99/54330, WO 99/58534, WO 99/61599, WO 99/65884, WO 99/65913, WO 99/66028, WO 99/67252, WO 99/67253 and WO 99/28324; cyclin dependent kinase inhibitors as found in WO 99/24416; and prenyl-protein transferase inhibitors as found in WO 97/30992 and WO 98/54966.

The compounds represented by formula I, as well as combinations thereof with the other anti-cancer/cytotoxic agents discussed above may also be formulated or co-administered with other therapeutic agents that are selected for their particular usefulness in providing certain therapies associated with the aforementioned conditions. For example, the compounds of the invention may be formulated with agents to prevent nausea, hypersensitivity, and gastric irritation, such as antiemetics, and H1 and $H_2$ antihistamines. The compounds of the present invention may also be formulated with antioangiogenesis compounds, topoisomerase inhibitors and antibody formulations.

Compounds of the present invention may also be used in combination with angiogenesis antagonists. These include inhibitors of epidermal growth factor (EGF), EGF family kinases (e.g., EGF tyrosine kinases), matrix metalloproteinase (MMPs), vascular endothelial growth factor receptor (VEGFR), fibroblast growth factor receptor (FGFR) and methionine adaptor protein 2 (Met AP2). Preferred angiogenesis antagonists also include antibodies directed to angiogenesis factors.

Representative examples of these classes of angiogenesis antagonists include, but are not limited to, indolinethiones, pyridopyrimidines, quinoazolines, phenyl-pyrrolo-pyrimidines, trastuzumab, IMC-C225, AG 1571 (SU 5271), SU 5416, SU 6668, Interferon-alpha, Interleukin-12, IM 862, EMD-121974, calcium influx inhibitor (CAI), neomycin, squalamine, endostatin, SI-27, MMI-166, marimastat, BAY-129556, prinomastat (AG-3340), metastat (COL-3), CGS-27023A and BMS-275291.

The above-discussed therapeutic agents, when employed in combination with the compounds represented by formula I, may be used in their usual therapeutic dosage as given, for example, in the *Physician's Desk Reference* (56$^{th}$ ed., 2002) or as otherwise determined by the medical practitioner.

Routes of Administration

The compounds represented by formula I may be administered by any suitable means, for example, orally, such as in the form of tablets, capsules, granules or powders; sublingually; buccally; parenterally, as sterile injectable aqueous or non-aqueous solutions or suspensions, by subcutaneous, intravenous, intramuscular, or intrasternal injection or infusion techniques; nasally, such as by inhalation spray; topically, such as in the form of a cream or ointment; or rectally such as in the form of suppositories; in dosage unit formulations containing non-toxic, pharmaceutically acceptable carriers or vehicles. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as a tablet, capsule, solution or suspension containing about 1 to about 500 mg per unit dosage of a compound or mixture of compounds represented by formula I or in a topical form containing, for example, 0.01 to 5% by weight compound represented by formula I, one to five treatments per day. Particular embodiments include, but are not limited to, 1 mg, 5 mg, 10 mg, 25 mg, 100 mg, 250 mg and 500 mg unit dosage forms.

In specific embodiments, it may be desirable to administer one or more compounds or pharmaceutical compositions of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of the primary cancer, metastasis, or solid tumor.

Determination of in vivo and in vitro Activity

The compounds of the present invention can be demonstrated to inhibit primary cancer, metastasis tumor cell proliferation, solid tumor proliferation, cell transformation and tumorigenesis in vitro and in vivo using a variety of assays known in the art, or described herein (Borzilleri et al., *J. Amer. Chem. Soc.*, Vol. 122, 8890 (2000); Lee et al., *An Epothilone Analog Possessing Potent Activity Against Paclitaxel-Sensitive and-Resistant Human Tumors* Book of Abstracts, 91$^{st}$ Annual Meeting of the American Association for Cancer Research, San Francisco, Calif., Apr. 1–5, 2000; American Association for Cancer Research, Philadelphia, Pa., 2000, LB-34; Lee et al., *Clin. Cancer Res.*, Vol. 7, 1429 (2001)). Such activity can be demonstrated in an in vitro assay by contacting the compounds of the present invention with human cancer cells. In general, human cancer cells are exposed to varying concentrations of the compounds of the present invention, followed by measuring cell survival relative to controls (Borzilleri et al., *Id.*). Such assays may use cells of a cancer cell line, or cells from a patient. Many assays well-known in the art can be used to assess such survival and/or growth; for example, cell proliferation can be assayed by measuring ($^3$H)-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc).

The compounds of the present invention can also be demonstrated to alter cell-proliferation in cultured cells in vitro using methods which are well known in the art. Specific examples of cell-culture models for primary brain cancer and brain metastasis include, but are not limited to, those found in the following U.S. Pat. Nos. 6,194,158; 6,051,376 and 6,071,696, each of which is incorporated herein by reference.

The compounds of the present invention can also be demonstrated to inhibit cell transformation (or progression to malignant phenotype) in vitro. In this embodiment, cells with a transformed cell phenotype are contacted with one or more compounds of the present invention, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, *General Virology,* 3d Ed., John Wiley & Sons, New York, pp. 436–446).

Loss of invasiveness or decreased adhesion may also be used to demonstrate the anti-cancer effects of the compounds of the present invention. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state. Loss of invasiveness may be measured by a variety of techniques known in the art including, for example, induction of E-cadherin-mediated cell-cell adhesion. Such E-cadherin-mediated adhesion can result in phenotypic reversion and loss of invasiveness (Hordijk et al., *Science,* Vol. 278, 1464–66 (1997)).

The compounds of the present invention can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in *Harrison's Principals of Internal Medicine,* 13th Ed., Isselbacher et al., eds., McGraw-Hill, N.Y., p. 1814, and Lovejoy et al., 1997, *J. Pathol.* 181:130–135. In particular, the utility of the compounds of the present invention can be demonstrated via its effects on human tumor xenografts in athymic mice (Lee et al., *An Epothilone Analog Possessing*

Potent Activity Against Paclitaxel-Sensitive and-Resistant Human Tumors Book of Abstracts, 91$^{st}$ Annual Meeting of the American Association for Cancer Research, San Francisco, Calif., Apr. 1–5, 2000; American Association for Cancer Research, Philadelphia, Pa., 2000, LB-34; Lee et al., Clin. Cancer Res., Vol. 7, 1429 (2001)). Further, general animal models applicable to many types of cancer have been described, including, but not restricted to, the p53-deficient mouse model (Donehower, 1996, Semin. Cancer Biol. 7:269–278), the Min mouse (Shoemaker et al., 1997, Biochem. Biophys. Acta, 1332:F25-F48), and immune responses to tumors in rat (Frey, 1997, Methods, 12:173–188).

For example, a compound of the present invention can be administered to a test animal, preferably a test animal predisposed to develop a primary tumor, and the test animal subsequently examined for an decreased incidence of tumor formation in comparison with controls not administered the compound. Alternatively, a compound of the present invention can be administered to test animals having primary tumors (e.g., animals in which tumors have been induced by introduction of malignant, neoplastic, or transformed cells, or by administration of a carcinogen) and subsequently examining the tumors in the test animals for tumor regression in comparison to control animals not administered the compound. Additional in vitro assays are described in the examples below.

GENERAL METHODS OF PREPARATION

Compounds of the invention can be prepared from the starting compounds designated and by the general methods described in the following schemes. All substituents are as defined in the schemes that follow or as defined above.

Compounds represented by formula I can be prepared as shown in Scheme 1.

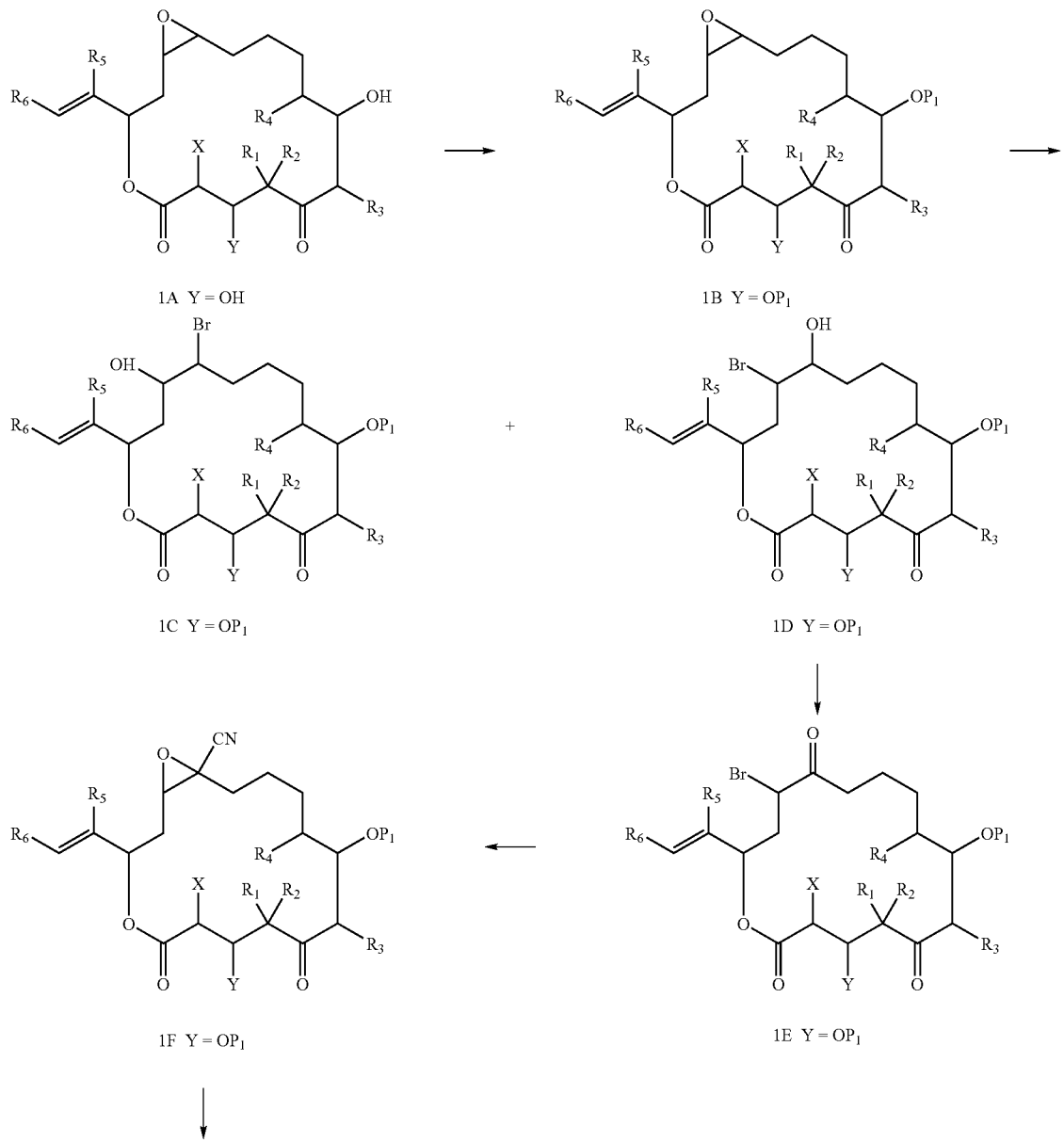

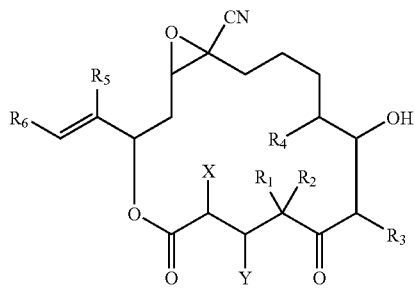

1G Y = OH

Compounds represented by formula 1A are known materials and can be obtained by a fermentation process as described, for example, in Hofle, G., et al, *Angew. Chem. Int. Ed. Engl.*, Vol. 35, No. 13/14, 1567–1569 (1996); by semi-synthesis from known epothilone starting materials as described, for example, by Vite, G., et al., in WO 99/02514 or Borzilleri et al., *J. Amer. Chem. Soc.*, Vol. 122, 8890 (2000); or by total synthesis from known starting materials as described, for example, by Nicolaou, K. C., et. al, *Angew. Chem., Int. Ed.*, Vol. 37(15), 2014–2045 (1998) or Danishefsky, S. J. et al., *Angew. Chem. Int. Ed. Engl.*, Vol. 35, 2801 (1996).

An exemplary synthesis is as follows. A compound represented by formula 1B, where P1 is a hydroxyl protecting group such as triethylsilyl, can be prepared from compounds represented by formula 1A by methods known to those skilled in the art such as described, for example, by Corey, E. J. and Venkateswarlu, A., *J. Am. Chem. Soc.*, 94, 6190 (1972). Compounds represented by formulae 1C and 1D can be prepared from by reacting a compound represented by formula 1B with magnesium bromide diethyl etherate in dichloromethane. A compound represented by formula 1E can be prepared by pyridinium chlorochromate oxidation of a compound represented by formula 1D in dichloromethane as described, for example, by White, J. D., et al., *J. Org. Chem.*, 12, 3600 (1995). A compound represented by formula 1F can be prepared from a compound represented by formula 1E using potassium cyanide and 18-crown ether-6 in tetrahydrofuran at 40° C. Deprotection of the resulting compound represented by formula 1F can be carried out using, for example, when $P_1$ is a triethylsilyl group, a 20% solution of trifluoroacetic acid in methylene chloride as described by Nicolaou, K. C., et al., *J. Am. Chem. Soc.*, Vol. 119, No. 34, 7960–7973 (1997), to afford a compound represented by formula I (1G). When P1 is a protecting group other than triethylsilyl, deprotection methods known in the art can be used, for example, as described by T. W. Greene and P. G. M. Wuts, *Protective Groups in Organic Synthesis*, John Wiley & Sons, Inc., New York, 10–142 (1991).

Scheme 2

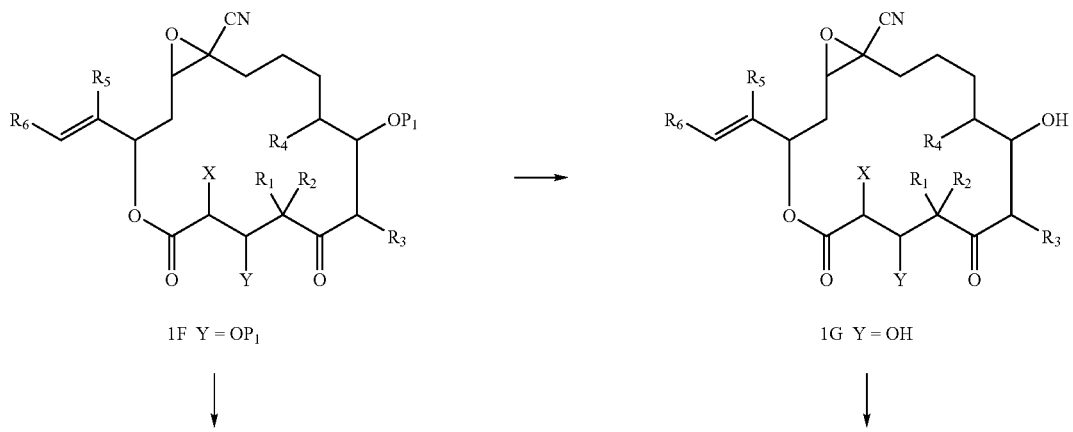

1F Y = OP₁            1G Y = OH

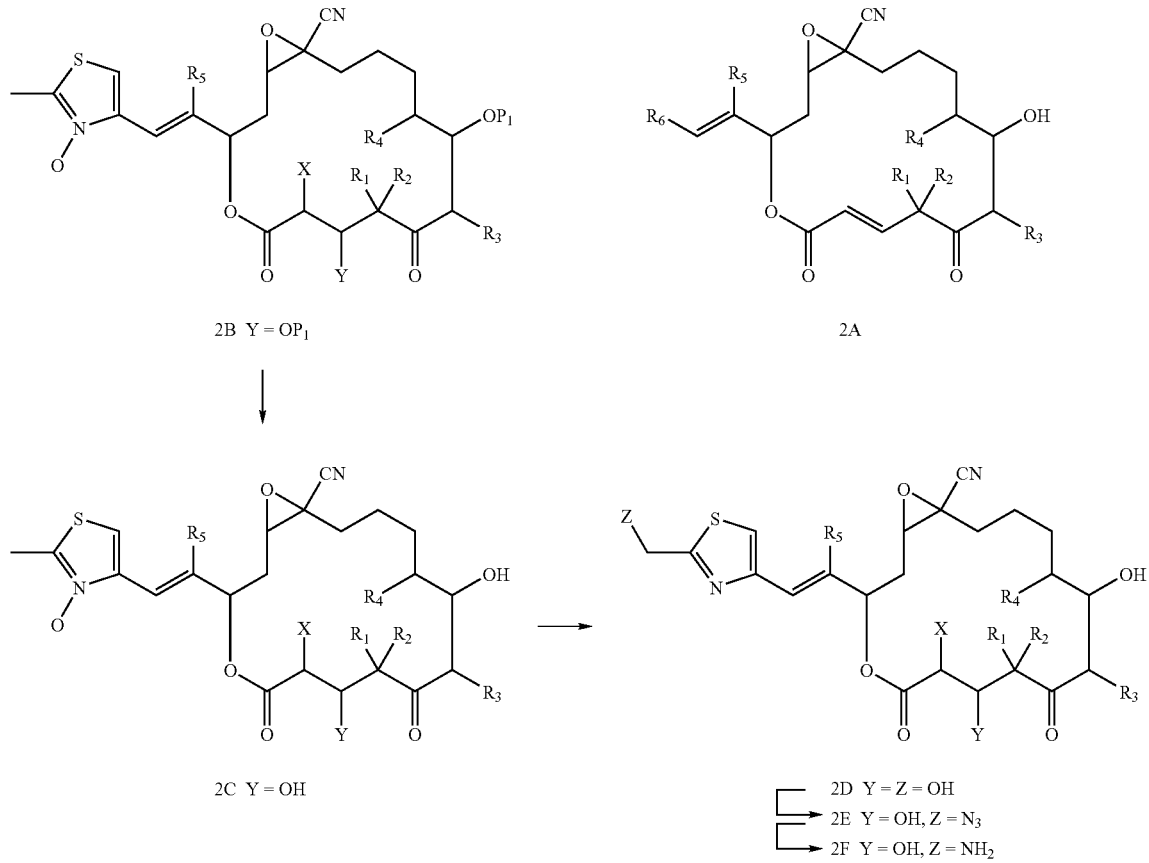

As illustrated in Scheme 2, compounds represented by formula I where X and Y together make a carbon—carbon bond (2A) can be prepared from a compound represented by formula 1G by the method described by Hofle (WO 97/19086).

Compounds represented by formula I where $R_6$ is a N-oxido-2-methylthiazolyl group (2C) can be prepared from compounds represented by formula 2B where $P_1$ is a hydroxyl protecting group, such as triethylsilyl, by methods known in the art. A compound represented by formula 2B can be prepared by oxidation of a compound represented by formula 1F, where $R_6$ is a 2-methylthiazolyl group, according to the method of Hofle, see *Angew. Chem., Int. Ed.*, 38(13/14), 1971–1974 (1999).

Compounds represented by formula I where $R_6$ is a 2-hydroxymethylthiazolyl group (2D) can be prepared by a rearrangement of the N-oxide using trifluoroacetic anhydride, analogous to the method described by Hofle (Id.)

Compounds represented by formula I where $R_6$ is a 2-azidomethylthiazolyl group (2E) can be prepared by reacting a compound represented by formula 2D with diphenylphosphoryl azide (see U.S. Pat. No. 6,262,094, incorporated by reference herein).

Compounds represented by formula I where $R_6$ is a 2-aminomethylthiazolyl group (2F) can be prepared by reducing the corresponding compound represented by formula 2E using a reducing agent, such as trimethylphosphine (see U.S. Pat. No. 6,262,094).

EXAMPLES

The following non-limiting examples serve to illustrate the practice of the invention.

Example 1

Preparation of [1S, 5S, 6S, 7R, 10S, 14S(E), 16S]-1-Cyano-6,10-dihydroxy-5,7,9,9-tetramethyl-14-[1-methyl-2-(2-methyl-4-thiazolyl)ethenyl]-13,17-dioxabicyclo[14.1.0]heptadecane-8,12-dione.

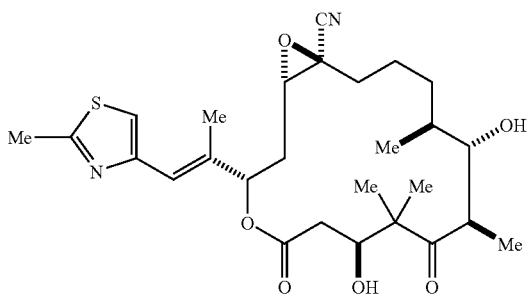

Compound A: [1S-[1R*,3R*(E),7R*,10S*,11R*,12R*,16S*]]-7,11-Bistriethylsilyloxy-8,8,10,12-tetramethyl-3-[1-methyl-2-(2-methyl-4-thiazolyl) ethenyl]-4,17-dioxabicyclo[14.1.0]heptadecane-5,9-dione.

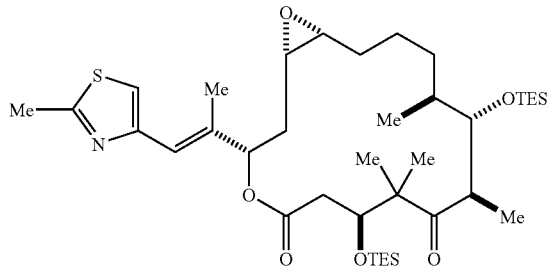

Triethylsilyl chloride (25 mL, 149 mmol) was added to epothilone A (10.39 g, 21 mmol), N,N-diisopropylethylamine (55 mL, 315 mmol), and imidazole (7.15 g, 105 mmol) in dimethyl formamide (75 mL) at 25° C. The reaction mixture was heated to 55° C. for 6.5 hours and concentrated in vacuo. The residue was then diluted with dichloromethane (100 mL) and the organic extracts were washed with a saturated aqueous solution of sodium bicarbonate (75 mL), dried over sodium sulfate and concentrated in vacuo. The residue was purified by flash chromatography (SiO$_2$, 0–15% ethyl acetate/hexanes gradient elution) to yield Compound A as a white solid (15.1 g, >95%). MS(ESI$^+$):(M+H)$^+$722.

Compound B: [4S-[4R*,7S*,8R*,9R*,13S*,14S*,16R*(E)]]-14-Bromo-4,8-bistriethylsilyloxy-13-hydroxy-5,5,7,9-tetramethyl-16-[1-methyl-2-(2-methyl-4-thiazolyl)ethenyl]-1-oxacyclohexadecane-2,6-dione.

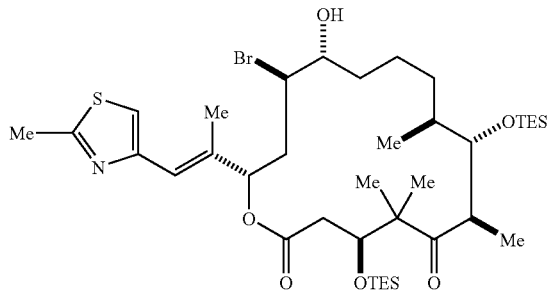

To a solution of Compound A from above (2.0 g, 2.8 mmol) in dichloromethane (30 mL) at −20° C. under argon was added magnesium bromide diethyl etherate (MgBr$_2$.OEt$_2$) in three 1.1 g. portions (12 mmol total) at two hour intervals while maintaining an internal temperature between −15° C. and −5° C. After seven hours, the reaction mixture was quenched with pH 7 phosphate buffer (40 mL) and brine (40 mL), extracted with three 100 mL portions of ethyl acetate, dried over sodium sulfate and concentrated in vacuo. The residue was purified by flash chromatography (SiO$_2$, 10–20% ethyl acetate/hexanes gradient elution) to afford Compound B as a white solid (1.0 g, 45%} (67% based on 0.6 g of recovered starting material; <2% of the other C$_{13}$—OH/C$_{12}$—Br regioisomer was detected). MS (ESI$^+$): (M+H)$^+$802.

Compound C: [4S-[4R*,7S*,8R*,9R*,14S*,16R*(E)]]-14-Bromo-4,8bistriethylsilyloxy-5,5,7,9-tetramethyl-16-[1-methyl-2-(2-methyl-4-thiazolyl)ethenyl]-1-oxacyclohexadecane-2,6,13-trione.

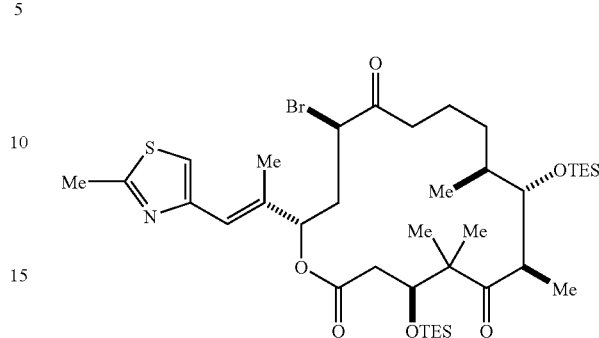

Pyridinium chlorochromate (320 mg, 1.48 mmol), pyridine (0.3 mL, 3.7 mmol), and a minor amount of crushed 4A molecular sieves was added to a solution of Compound B from above (300 mg, 0.37 mmol) in dichloromethane (3 mL). After five hours, the reaction mixture was diluted with 50 mL of dichloromethane, filtered through a short plug of silica gel, concentrated and purified by flash chromatography (SiO$_2$, 0–5% ethyl acetate/hexanes gradient elution) to isolate Compound C as a white solid (273 mg, 92%). MS (ESI$^+$): (M+H)$^+$800.

Compound D: [1S, 5S, 6S, 7R, 10S, 14S(E), 16S]-6,10-Bistriethylsilyloxy-1-cyano-5,7,9,9-tetramethyl-14-[1-methyl-2-(2-methyl-4-thiazolyl)ethenyl]-13,17-dioxabicyclo[14.1.0]heptadecane-8,12-dione.

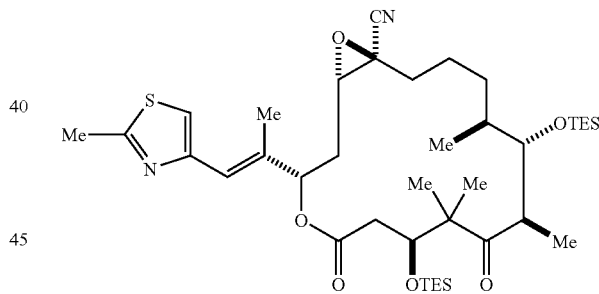

Potassium cyanide (153 mg, 2.35 mmol) and a minor amount of 18-crown ether-6 were added to a solution of Compound C from above (755 mg, 0.94 mmol) in anhydrous tetrahydrofuran (8 mL). The reaction mixture was stirred at 25° C. for four hours, concentrated in vacuo and the residue purified by flash chromatography (SiO$_2$, 10%-30% ethyl acetate/hexanes gradient elution) to afford Compound D as a yellow oil (305 mg, 49%). MS (ESI$^+$): (M+H)$^+$747.

Title compound: To a solution of Compound D from above (61 mg, 0.08 mmol) in dichloromethane (1 mL) at −15° C. was added a 20% solution of trifluoroacetic acid in dichloromethane (1 mL). The reaction mixture was stirred for thirty minutes, then quenched by the addition of an aqueous saturated solution of sodium bicarbonate (1 mL). The organic phase was extracted with three 10 mL portions of trichloromethane, dried over sodium sulfate, and concentrated in vacuo. The residue was purified by flash chromatography (SiO$_2$,20%–60% ethyl acetate/hexanes gradient elution) to afford the title compound as a white solid (45 mg, 98%). MS (ESI+): (M+H)+519.

Example 2

[1S, 5S, 6S, 7R, 10S, 14S(E), 16S]-6,10-Bistriethylsilyloxy-1-cyano-5,7,9,9-tetramethyl-14-[1-methyl-2-(2-methyl-4-thiazolyl)ethenyl]-13,17-dioxabicyclo [14.1.0]heptadecane-8,12-dione, N-oxide.

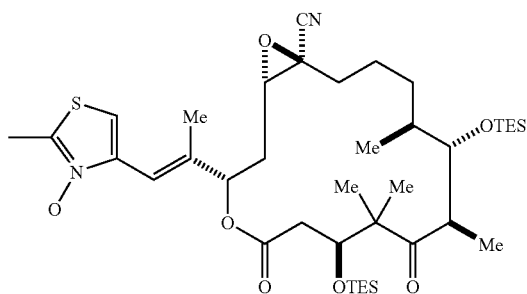

A solution of Compound D from Example 1 (62 mg, 0.083 mmol) in dichloromethane (1 mL) was treated with 3-chloroperoxybenzoic acid (25 mg, 55–86%, 0.09 mmol). The mixture was allowed to stir for 4 hours. The reaction mixture was quenched with saturated aqueous sodium bicarbonate (1 mL) and extracted with three 10 mL portions of ethyl acetate and one 10 mL portion of trichloromethane. The combined organic extracts were washed with 5% aqueous sodium sulfite (10 mL), dried over sodium sulfate and concentrated in vacuo. The crude reaction product was purified by flash chromatography (SiO$_2$, 5% MeOH/CHCl$_3$) to provide the title compound (41.5 mg, 65.6%). MS (ESI+): 631 (M+H)+

Example 3

[1S, 5S, 6S, 7R, 10S, 14S(E), 16S]-1-Cyano-6,10-dihydroxy-5,7,9,9-tetramethyl-14-[1-methyl-2-(2-methyl-4-thiazolyl)ethenyl]-13,17-dioxabicyclo[14.1.0]heptadecane-8,12-dione, N-oxide.

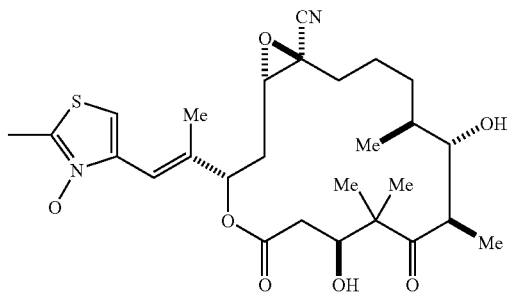

A solution of the compound prepared in Example 2 (41.0 mg, 0.054 mmol) in dichloromethane (1 mL) was cooled to −20° C. and treated with trifluoroacetic acid (1 mL, 20% in dichloromethane). The mixture was allowed to slowly warm to room temperature over 1 hour. The reaction mixture was quenched with saturated aqueous sodium bicarbonate (10 mL) and extracted with three 10 mL portions of ethyl acetate and one 10 mL portion of trichloromethane. The combined organic extracts were dried over sodium sulfate and con-centrated in vacuo. The crude reaction product was purified by flash chromatography (SiO$_2$, 50%–100% ethyl acetate/hexanes gradient elution then 2% MeOH/CHCl$_3$) to provide the title compound (23.8mg, 82%) as a white solid. MS (ESI+): 535 (M+H)+

Example 4

[1S, 5S, 6S, 7R, 10S, 14S(E),16S]-1-Cyano-6,10-dihydroxy-5,7,9,9-tetramethyl-14-[1-methyl-2-(2-hydroxymethyl-4-thiazolyl)ethenyl]-13,17-dioxabicyclo [14.1.0]heptadecane-8,12-dione.

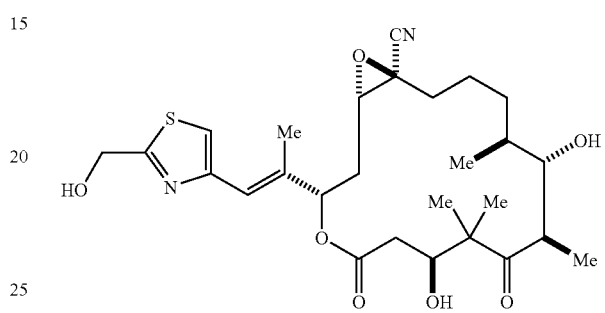

To a solution of the compound prepared in Example 3 (442 mg, 0.827 mmol) in dichloromethane (16.5 mL) in a sealed tube was added 2,6-lutidine (769 mL, 6.62 mmol) and trifluoroacetic anhydride (813 mL, 5.78 mmol) and the reaction was heated at 70° C. for 30 min. The mixture was allowed to cool and the solvent was removed under a stream of argon, followed by concentration to a yellow oil in vacuo. The residue was dissolved in methanol (11 mL) and ammonium hydroxide was added (133 mL, 28% in water). The mixture was heated at 45° C. for 30 min. The crude product was concentrated in vacuo and chromatographed (SiO$_2$, 50%–100% ethyl acetate/hexanes gradient elution) to provide the title compound (364 mg, 82%). MS (ESI+): 535 (M+H)+ as a yellow solid along with trifluoroacetate byproduct (10 mg, 2.2%). MS (ESI+): 630 (M+H)+.

Example 5

[1S, 5S, 6S, 7R, 10S, 14S(E), 16S]-1-Cyano-6,10-dihydroxy-5,7,9,9-tetramethyl-14-[1-methyl-2-(2-azidomethyl-4-thiazolyl)ethenyl]-13,17-dioxabicyclo [14.1.0]heptadecane-8,12-dione.

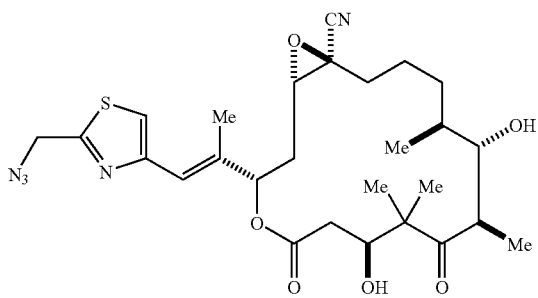

To a stirred solution of the compound prepared in Example 4 (364 mg, 0.68 mmol) in tetrahydrofuran (7.5 mL) at 0° C. under argon was added diphenylphosphoryl azide (176 mL, 0.816 mmol). The mixture was stirred for 10 min., 1,8-diazabicyclo [5.4.0]undec-7-ene (122 mL, 0.816 mmol) was then added and the mixture was stirred at 0° C. for 4 hours. The mixture was warmed slowly to 25° C. and stirred for 12 hours. The reaction mixture was concentrated in vacuo, and the residue was purified (SiO$_2$, 30%–50% ethyl acetate/hexanes gradient elution) to provide the title compound (125 mg, 33%). MS (ESI$^+$): 560.2 (M+H)$^+$.

Example 6

[1S, 5S, 6S, 7R, 10S, 14S(E), 16S]-1-Cyano-6,10-dihydroxy-5,7,9,9-tetramethyl-14-[1-methyl-2-(2-aminomethyl-4-thiazolyl)ethenyl]-13,17-dioxabicyclo[14.1.0]heptadecane-8,12-dione.

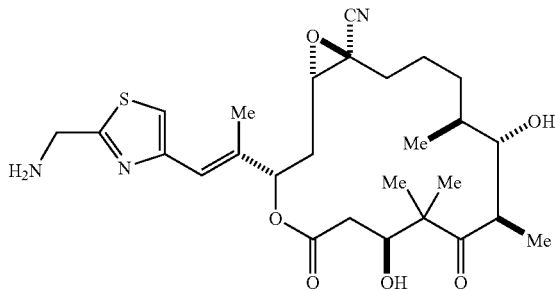

To a stirred solution of the compound prepared in Example 5 (117 mg, 0.21 mmol) in tetrahydrofuran (2 mL) under argon was added trimethylphosphine (231 mL, 0.23 mmol, 1M in tetrahydrofuran) and the reaction was stirred at room temperature for 1 hour, then quenched with ammonium hydroxide (325 mL, 28% in water). The mixture was stirred for an additional 30 min. The volatiles were removed in vacuo and the crude material was purified (SiO$_2$, ethyl acetate, then 1–10% MeOH/CHCl$_3$ gradient elution). The material obtained was dissolved in ethyl acetate (20 mL) and washed twice with 20 mL portions of saturated aqueous sodium bicarbonate. The solution was dried over sodium sulfate and dried in vacuo to provide the title compound (100.5 mg, 89%) as a white solid. MS (ESI$^+$): 534.2 (M+H)$^+$.

The following compounds can be made following the reaction schemes previously disclosed:
 [1S, 5S, 6S, 7R, 10S, 14S(E), 16S]-1-Cyano-6,10-dihydroxy-5,7,9,9-tetramethyl-14-[1-methyl-2-(2-methyl-4-thiazolyl)ethenyl]-13,17-dioxabicyclo[14.1.0]heptadecane-8,12-dione;
 [1S, 5S, 6S, 7R, 10S, 14S(E), 16S]-6,10-Bistriethylsilyloxy-1-cyano-5,7,9,9-tetramethyl-14-[1-methyl-2-(2-methyl-4-thiazolyl)ethenyl]-13,17-dioxabicyclo [14.1.0]heptadecane-8,12-dione, N-oxide;
 [1S, 5S, 6S, 7R, 10S, 14S(E), 16S]-1-Cyano-6,10-dihydroxy-5,7,9,9-tetramethyl-14-[1 -methyl-2-(2-methyl-4-thiazolyl)ethenyl]-13,17-dioxabicyclo[14.1.0]heptadecane8,12-dione, N-oxide;
 [1S, 5S, 6S, 7R, 10S, 14S(E), 16S]-1-Cyano-6,10-dihydroxy-5,7,9,9-tetramethyl-14-[1-methyl-2-(2-hydroxymethyl-4-thiazolyl)ethenyl]-13,17-dioxabicyclo[14.1.0] heptadecane-8,12-dione;
 [1S, 5S, 6S, 7R, 10S, 14S(E), 16S]-1-Cyano-6,10-dihydroxy-5,7,9,9-tetramethyl-14-[1-methyl-2-(2-azidomethyl-4-thiazolyl)ethenyl]-13,17-dioxabicyclo[14.1.0] heptadecane-8,12-dione; and
 [1S, 5S, 6S, 7R, 10S, 14S(E), 16S]-1-Cyano-6,10-dihydroxy-5,7,9,9-tetramethyl-14-[1-methyl-2-(2-aminomethyl-4-thiazolyl)ethenyl]-13,17-dioxabicyclo[14.1.0] heptadecane-8,12-dione.

Example 7

In Vitro Tubulin Polymerization Assay

Twice cycled (2×) calf brain tubulin is prepared following the procedure of Williams and Lee (Williams, R. C., Jr. and Lee, J. C., *Methods in Enzymology,* 85, 376–385 (1982)) and stored in liquid nitrogen before use. Quantification of tubulin polymerization potency is accomplished following a modification of the procedure described by Swindell, C. S., et al., in *J. Med. Chem.,* 34, 1176–1184 (1991). The modification used, in part, results in the expression of tubulin polymerization potency as an effective concentration for any given compound.

In accordance with this method, differing concentrations of a compound to be studied are mixed with a polymerization buffer (0.1 M MES [2(4-morpholino) ethanesulfonic acid], 1 mM EGTA [ethyleneglycol-bis-(beta-aminoethyl ether) N,N'-tetraacetic acid], 0.5 mM MgCl$_2$, pH 6.6) and added to the prepared tubulin, also mixed with a corresponding polymerization buffer, both mixtures being at 37° C. The resulting mixture is then placed in the microcuvette wells of an ultraviolet spectrophotometer (Beckman Instruments, Model DU 7400). Generally, a final microtubule protein concentration of 1.0 mg/mL and compound concentrations of 2.5, 5.0, and 10 μM are used in this procedure. Initial slopes of OD change measured every ten seconds are calculated by the software program accompanying the spectrophotometer after initial and final times of the linear region encompassing at least three time points are manually measured. Under the prescribed conditions linear variances are generally <10$^{-6}$, slopes range from 0.03 to 0.002 absorbance units/minute, and the maximum absorbance is 0.15 absorbance units.

Effective concentration (EC$_{0.01}$) is defined as the interpolated concentration capable of inducing an initial slope of 0.01 OD/minute rate and is calculated using the formula: EC$_{0.01}$=concentration/slope EC$_{0.01}$ values are expressed as the mean with standard deviation obtained from three different concentrations. EC$_{0.01}$ values for the compounds of the invention range from 0.01 to 1000 μM.

Example 8

In Vitro Cytotoxicity Assay

Cytotoxicity is assessed in HCT-116 human colon carcinoma cells by the MTS (3-(4,5-dimethylthiazol-2-yl)-5-(3-carboxymethoxyphenyl)-2-(4-sulphenyl)-2H-tetrazolium, inner salt) assay of Riss et al., *Mol. Biol. Cell,* 3(Suppl.), 184 (1992).

According to this assay, the HCT-116 human colon carcinoma cells are plated at 4,000 cells/well in 96 well microtiter plates. Twenty-four hours after plating, the compound(s) to be studied are added and serially diluted. The cells are then incubated at 37° C. for 72 hours. After incubation, MTS (at a final concentration of 333 μg/mL) and an electron coupling agent (25 μM phenazine methosulfate) are added to the cells.

A dehydrogenase enzyme in live cells reduces the MTS to a form that absorbs light at 492 nM, which can be quantified spectrophotometrically. Absorbance is directly proportional to the number of live cells, i.e. the greater the absorbance, the greater the number of live cells present. Results are expressed as an $IC_{50}$, which is the drug concentration required to inhibit cell proliferation (i.e., absorbance at 450 nM) to 50% of that of untreated control cells.

In a preferred embodiment, $IC_{50}$ values for compounds of the invention are in the range of 0.01 to 1000 nM in the in vitro cytotoxicity assay, however, compounds with activity outside of this range are included in certain embodiments.

All references with respect to synthetic, preparative and analytic procedures are incorporated herein by reference as if set forth at length herein.

The present invention may be embodied in other specific forms without departing from the spirit or essential attributes thereof and, accordingly, reference should be made to the appended claims, rather than to the foregoing specification, as indicating the scope of the invention.

What is claimed is:

1. A compound represented by formula I:

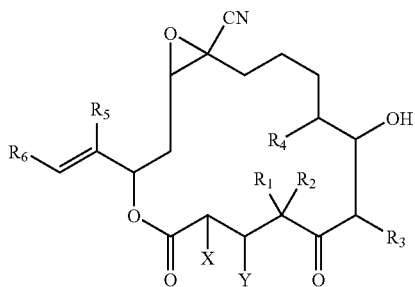

wherein:

$R_1$, $R_2$, $R_3$, $R_4$, and $R_5$ are independently selected from hydrogen and lower alkyl;

$R_6$ is optionally-substituted thiazolyl;

X is hydrogen and Y is hydroxy, or X and Y taken together represent a carbon-carbon bond;

and steroisomers, pharmaceutically acceptable salts, solvates and/or hydrates thereof.

2. The compound of claim 1 wherein $R_1$, $R_2$, $R_3$, $R_4$ and $R_5$ are each methyl.

3. The compound of claim 2 wherein:

$R_6$ is selected from the group consisting of:

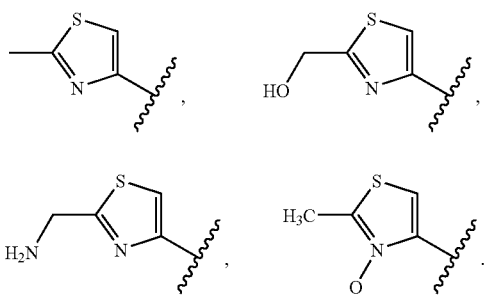

4. The compound of claim 1 wherein X is hydrogen and Y is hydroxy.

5. The compound of claim 1 wherein said compound is selected from the group consisting of:

[1S, 5S, 6S, 7R, 10S, 14S(E), 16S]-1-Cyano-6,10-dihydroxy-5,7,9,9-tetramethyl-14-[1-methyl-2-(2-methyl-4-thiazolyl)ethenyl]-13,17-dioxabicyclo[14.1.0]heptadecane-8,12-dione;

[1S, 5S, 6S, 7R, 10S, 14S(E), 16S]-1-Cyano-6,10-dihydroxy-5,7,9,9-tetramethyl-14-[1-methyl-2-(2-hydroxymethyl-4-thiazolyl)ethenyl]-13,17-dioxabicyclo[14.1.0]heptadecane-8,12-dione;

[1S, 5S, 6S, 7R, 10S, 14S(E), 16S]-1-Cyano-6,10-dihydroxy-5,7,9,9-tetramethyl-14-[1-methyl-2-(2-azidomethyl-4-thiazolyl)ethenyl]-13,17-dioxabicyclo[14.1.0]heptadecane-8,12-dione; and

[1S, 5S, 6S, 7R, 10S, 14S(E), 16S]-1-Cyano-6,10-dihydroxy-5,7,9,9-tetramethyl-14-[1-methyl-2-(2-aminomethyl-4-thiazolyl)ethenyl]-13,17-dioxabicyclo[14.1.0]heptadecane-8,12-dione;

and pharmaceutically acceptable salts, solvates or hydrates thereof.

6. A pharmaceutical composition comprising as an active ingredient at least one compound of claim 1, or a pharmaceutically acceptable salt, solvate, and/or thereof, and one or more pharmaceutically acceptable carriers, excipients and/or diluents.

7. The pharmaceutical composition of claim 6 additionally comprising as a further active ingredient a therapeutic agent useful in the treatment of cancer or other proliferative diseases.

8. The pharmaceutical composition of claim 7 wherein said therapeutic agent useful in the treatment of cancer or other proliferative diseases is selected from the group consisting of adriamycin, cisplatin, carboplatin, cimetidine, carminomycin, mechlorethamine hydrochloride, pentamethylmelamine, thiotepa, teniposide, cyclophosphamide, chlorambucil, demethoxyhypocrellin A, melphalan, ifosfamide, trofosfamide, Treosulfan, podophyllotoxin or podophyllotoxin derivatives, etoposide phosphate, teniposide, etoposide, leurosidine, leurosine, vindesine, 9-aminocamptothecin, camptoirinotecan, crisnatol, Chloroambucil, megestrol, methopterin, mitomycin C, ecteinascidin 743, busulfan, carmustine (BCNU), lomustine (CCNU), lovastatin, 1-methyl-4-phenylpyridinium ion, semustine, staurosporine, streptozocin, thiotepa, phthalocyanine, dacarbazine, aminopterin, methotrexate, trimetrexate, thioguanine, mercaptopurine, fludarabine, pentastatin, cladribin, cytarabine (ara C), porfiromycin, 5-fluorouracil, 6-mercaptopurine, doxorubicin hydrochloride, leucovorin, mycophenoloc acid, daunorubicin, deferoxamine, floxuridine, doxifluridine, ratitrexed, idarubicin, epirubican, pirarubican, zorubicin, mitoxantrone, bleomycin sulfate, mitomycin C, actinomycin D, safracins, saframycins, quinocarcins, discodermolides, vincristine, vinblastine, vinorelbine tartrate, vertoporfin, paclitaxel, tamoxifen, raloxifene, tiazofuran, thioguanine, ribavirin, EICAR, estramustine, estramustine phosphate sodium, flutamide, bicalutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, verapamil, VP-16, altretamine, thapsigargin and topotecan.

9. A unit dosage form of a pharmaceutical composition comprising a compound of claim 1.

10. A sterile injectable unit dosage form of a pharmaceutical composition comprising a compound of claim 1.

11. The unit dosage form of claim 9 wherein said dosage form is lyophilized.

12. The unit dosage form of claim 10 wherein said dosage form is lyophilized.

13. A compound of claim 3 wherein X is hydrogen and Y is hydroxy.

14. A compound of claim 1 wherein:

$R_6$ is selected from the group consisting of:

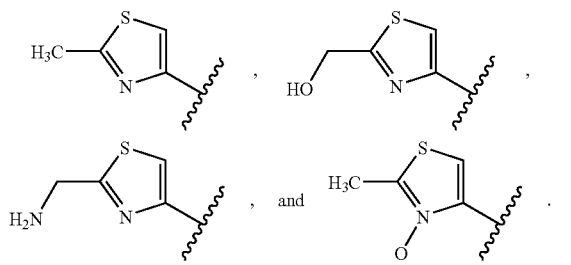

15. A compound of claim 14 wherein X is hydrogen and Y is hydroxy.

16. A pharmaceutical composition comprising as an active ingredient at least one compound of claim 3, or a pharmaceutically-acceptable salt, solvate, and/or hydrate thereof, and one or more pharmaceutically-acceptable carriers, excipients and/or diluents.

17. A pharmaceutical composition comprising as an active ingredient at least one compound of claim 13, or a pharmaceutically-acceptable salt, solvate, and/or hydrate thereof, and one or more pharmaceutically-acceptable carriers, excipients and/or diluents.

18. A pharmaceutical composition comprising as an active ingredient at least one compound of claim 14, or a pharmaceutically-acceptable salt, solvate, and/or hydrate thereof, and one or more pharmaceutically-acceptable carriers, excipients and/or diluents.

19. A pharmaceutical composition comprising as an active ingredient at least one compound of claim 15, or a pharmaceutically-acceptable salt, solvate, and/or hydrate thereof, and one or more pharmaceutically-acceptable carriers, excipients and/or diluents.

* * * * *

UNITED STATES PATENT AND TRADEMARK OFFICE
CERTIFICATE OF CORRECTION

PATENT NO.        : 7,211,593 B2
APPLICATION NO.   : 10/386059
DATED             : May 1, 2007
INVENTOR(S)       : Gregory D. Vite et al.

It is certified that error appears in the above-identified patent and that said Letters Patent is hereby corrected as shown below:

Claim 1:
    Column 29, line 44, change "steroisomers" to -- stereoisomers --.

Claim 3:
    Column 29, lines 53 to 57, change " 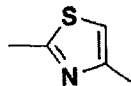 " to -- 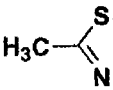 --.

Claim 3:
    Column 29, line 62, after " 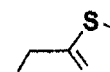 ", insert -- and --.

Claim 6:
    Column 30, line 23, after "and/or", insert -- hydrate --.

Signed and Sealed this

Sixteenth Day of March, 2010

David J. Kappos
*Director of the United States Patent and Trademark Office*